United States Patent [19]

Strickler et al.

[11] Patent Number: 5,455,333

[45] Date of Patent: Oct. 3, 1995

[54] PREPARATION OF METALLOCENES

[75] Inventors: Jamie R. Strickler; John M. Power, both of Baton Rouge, La.

[73] Assignee: Albemarle Corporation, Richmond, Va.

[21] Appl. No.: 106,596

[22] Filed: Aug. 16, 1993

[51] Int. Cl.$^6$ .............................. C07F 5/00; C07F 9/00; C07F 13/00; C07F 17/00

[52] U.S. Cl. ........................ 534/11; 556/43; 556/47; 556/52; 556/58; 556/136; 556/137; 556/140; 534/15

[58] Field of Search .................. 556/52, 43, 47, 556/52, 58, 136, 137, 140; 534/11, 15

[56] References Cited

U.S. PATENT DOCUMENTS

| | | | |
|---|---|---|---|
| 4,808,561 | 2/1989 | Welborn, Jr. | 502/104 |
| 5,189,192 | 2/1993 | LaPoint et al. | 556/11 |
| 5,200,537 | 4/1993 | Lee et al. | 556/11 |

FOREIGN PATENT DOCUMENTS

| | | | |
|---|---|---|---|
| 0416815 | 3/1991 | European Pat. Off. | C08F/10/00 |
| 0418044 | 3/1991 | European Pat. Off. | C08F/10/00 |
| 0468651 | 1/1992 | European Pat. Off. | C08F/4/74 |
| 0514828 | 11/1992 | European Pat. Off. | C07F/7/28 |
| 0520732 | 12/1992 | European Pat. Off. | C08F/10/00 |

OTHER PUBLICATIONS

J. Chem Soc., Commun., 1990, pp. 1470–1471, Luinstra et al., Lead Dichloride: a Mild Reagent for the Oxidation of Tervalent Titanium Compounds $(\eta^5-C_5Me_5)_2TiR$ to Monochloride derivatives $(\eta^5-C_5Me_5)_2TiR(Cl)$.

Inorganica Chimica Acta, 180 (1991) 153–160, pp. 153–160, Szymoniak, et al., Synthesis of bent titanocene metalloligands with the (diphenylphosphino)tetramethyl-cyclopentadienyl moiety. X–ray structure of $[(\eta^5-C_5Me_4PPh_2)_2TiCl_2]Mo(Co)_4$.

Pearson, A. J., Metallo–organic Chemistry, John Wiley and Sons, New York, 1985, pp. 114–116.

Gambarotta et al., Inorg. Chem., vol. 23, No. 12, pp. 1739–1747 (1984).

*Primary Examiner*—Porfirio Nazario-Gonzales
*Attorney, Agent, or Firm*—David M. Bunnell

[57] ABSTRACT

Metallocenes which are useful as olefin polymerization catalysts are prepared by reacting a compound of a metal of the group 4 to 10, lanthanide or actinide series of the Periodic Table of the Elements with a magnesium halide salt of a cyclopentadienyl containing ligand in the presence of an organic halide so as to form the metallocene while simultaneously raising the oxidation state of the metal.

9 Claims, No Drawings

PREPARATION OF METALLOCENES

This invention relates generally to the preparation of metallocenes which are useful as olefin polymerization catalysts and more specifically to a process for making metallocenes by metallizing cyclopentadienyl ligand salts with certain transition, lanthanide or actinide metal compounds while simultaneously raising the oxidation of the metal with an organic halide.

As known in the art, metallocenes can be prepared by reacting a metal compound of the formula $MX_n$ where M is the metal, n is an integer of 1 to 6, depending upon the valence of M, and X is independently an anionic ligand group or a neutral Lewis base ligand group having up to 30 non-hydrogen atoms such as hydride, halo, alkyl, aryl, silyl, germyl, aryloxy, alkoxy, amide, and siloxy, with an alkali metal or a magnesium halide salt of the cyclopentadienyl ligand in an ether solvent. In metals having multiple oxidation states, the valence of the transition metal can be selected to be one less than its desired valence in the final complex because a cleaner reaction is obtained. For example, it has been found that it is better to start with $TiCl_3$ and then to oxidize the complex with an oxidizing agent rather than to start with $TiCl_4$. Using $TiCl_4$ can result in the formation of a precipitate of $TiCl_3$ due to reduction by the ligand salt.

The oxidation of metallocenes of tervalent transition metals, so as to raise the oxidation state of the metal, using mild inorganic oxidizing agents have been disclosed, for example, by Lunestra et al. who disclose the use of $PbCl_2$ (*J. Org. Chem. Commun.*, 1990, pages 1470–1471) and in EP patent 416,815 which discloses the use of AgCl for this purpose to form a Ti (IV) complex from a Ti (III) complex. These oxidants, however, produce heavy metal by-products which present disposal problems and contaminate the product due to co-precipitation of the reduced metal with the product. On the other hand, the use of aqueous HCl as an oxidizing agent can result in decomposition of the metallocene product. European patent application 514,828 discloses the formation of tetravalent metallocenes by forming a tervalent metallocene followed by oxidation of the metallocene using an organic halide. We found that the formation of the metal complex followed by oxidation has the disadvantage of producing some alkoxide impurity due to partial oxidation of the metal by the preferred ether solvents prior to the treatment with the oxidizing agent. This impurity cannot be easily separated from the metallocene product and the presence of even a small amount of such impurity can be detrimental to its catalytic properties.

We have now found that such impurity formation can be avoided by conducting the alkyl halide oxidation of the transition metal at the same time that the metal-ligand complex is formed. The metallocenes, therefore, can be made in one step in high yields and improved purity.

In accordance with this invention there is provided a process for preparing a metallocene, said process comprising reacting a metal compound, wherein said metal has at least two oxidation states and is selected from the group consisting of Group 4 to 10 metals, and metals of the lanthanide, and actinide series of the Periodic Table of the Elements, with a magnesium halide salt of a cyclopentadienyl containing ligand in the presence of an organic halide so as to form said metallocene while simultaneously raising the oxidation state of said metal.

Metallocenes of metals of the Group 4–10, lanthanide and actinide series of the Periodic Table of the Elements which have more than one oxidation state such as Cr, Fe, Ce and U, and especially transition metals of Groups 4 and 5 of the new IUPAC notation for the Periodic Table such as Ti, V, and Nb, which are metal coordination complexes containing at least one cyclopentadienyl or substituted cyclopentadienyl containing ligand, are known. Such metallocenes, when activated, are useful as olefin polymerization catalysts.

Non-limiting examples of metallocenes which can be prepared by the process of the invention are described in European Patent Application 514,828 which was published on Nov. 25, 1992 and U.S. Pat. Nos. 5,200,537, and 4,808,561 whose disclosures are hereby incorporated by reference. Specific compounds include bis(pentamethylcyclopentadienyl)titanium dichloride, bis(indenyl)titanium dichloride, bis(methylcyclopentadienyl)titanium dichloride, racemic and meso dimethylsilanyl bridged bis(methylcyclopentadienyl)titanium dichloride, bis(cyclopentadienyl)titanium dichloride, bis(ethylcyclopentadienyl)methylvanadium chloride, bis(β-phenylpropylcyclopentadienyl)methyltitanium bromide, bis(methylcyclopentadienyl)methyltitanium bromide, racemic dimethylsilanyl bridged bis(indenyl)cerium dichloride, racemic ethylene bridged bis(indenyl)titanium dichloride, ($\eta^5$-indenyl)chromium trichloride, ($\eta^5$-$C_5Me_5$)titanium trichloride, bis(1,3-di(trimethylsilyl)cyclopentadienyl)thorium dichloride, bis(1,3-di(trimethylsilyl)cyclopentadienyl)uranium monochloride, bis(1,3-di(trimethylsilyl)cyclopentadienyl)uranium dichloride, bis(pentamethylcyclopentadienyl)thorium dichloride, bis(pentamethylcyclopentadienyl)uranium dichloride, (tert-butylamido)dimethyl(tetramethyl-$\eta^5$-cyclopentadienyl)-silanetitanium dichloride, (tert-butylamido)dimethyl(tetramethyl-$\eta^5$-cyclopentadienyl)silanechromium dichloride, (tert-butylamido)dimethyl(-$\eta^5$-cyclopentadienyl)silanetitanium dichloride, (tert-butylamido)dimethyl(tetramethyl-$\eta^5$-cyclopentadienyl)silanemethyltitanium bromide, (tert-butylamido)(tetramethyl-$\eta^5$-cyclopentadienyl)-1,2-ethanediyluranium dichloride, (tert-butylamido)(tetramethyl-$\eta^5$-cyclopentadienyl-1,2-ethanediyltitanium dichloride, (methylamido)(tetramethyl-$\eta^5$-cyclopentadienyl)-1,2-ethanediylcerium dichloride, (methylamido)(tetramethyl-$\eta^5$-cyclopentadienyl)-1,2-ethanediyltitanium dichloride, (ethylamido)(tetramethyl-$\eta^5$-cyclopentadienyl)methylenetitanium dichloride, (tert-butylamido)dibenzyl(tetramethyl-$\eta^5$-cyclopentadienyl)silanebenzylvanadium chloride, (benzylamido)dimethyl(indenyl)silanetitaniume dichloride, and (phenylphosphido)dimethyl(tetramethyl-$\eta^5$-cyclopentadienyl)silanebenzyltitanium chloride.

According to the process of the invention, the metallocenes are prepared by reacting a transition metal compound of the formula $MX_n$, where M is the metal, n is an integer of 1 to 6, depending upon the valence of M, and X is independently an anionic ligand group or a neutral Lewis base ligand group having up to 30 non-hydrogen atoms such as hydride, halo, alkyl, aryl, silyl, germyl, aryloxy, alkoxy, amide, and siloxy, with a magnesium halide salt of the cyclopentadienyl ligand in an ether solvent. Preferred metal compounds are metal halides in the form of their ether complexes such as $TiCl_3(THF)_3$. Preferably, the reactants are used in about equimolar portions up to about a 50% molar excess of the metal compound, which is the less expensive reagent, and the valence of the transition metal is selected to be one less than its desired valence in the final complex.

A magnesium halide salt (Grignard reagent) of the ligand is used in order to avoid side reactions between the ligand complex and the organic halide oxidizing agent. We have found that alkali metal salts of the ligand cannot be used in the process of the invention because they react with the organic halide oxidizing agent.

Numerous organic halides may be used for the oxidation according to the present invention. Examples include methyl chloride, methylene chloride, chloroform, carbon tetrachloride, 1,1,1-trichloroethane, tetrachloroethylene, 1-chloropropane, 1-chlorodecane, benzylchloride, chlorobenzene, or even a solution of polyvinylchloride dissolved in a suitable solvent. The corresponding bromine or iodine containing organic halides may also be used if desired. Preferred organic halides are $C_{1-12}$ alkylchlorides having from 1 to 10 chlorine atoms. Particularly preferred organic halides are methylchloride, methylene chloride and chloroform.

The quantity of organic halide employed in the oxidation is suitably at least one equivalent based on halogen content for each mole of metal compound to be oxidized. A large excess of organic halide can also be used without detriment, with the excess organic halide acting as a solvent for the reaction. Preferred ratios of organic halide (equivalents based on halogen content: moles metal compound) are from 1:1 to 10,000:1, preferably 1:1 to 100:1, most preferably 1:1 to 2:1.

The reaction is preferably carried out in an inert solvent to facilitate the separation of the product and salt by-product. The preferred solvents for use in the reaction are ethers such as, for example, diethyl ether, 1,2-dimethoxyethane and the like, and, most preferably tetrahydrofuran. The solvent can also include a hydrocarbon solvent such as, for example, hexane, cyclohexane, heptane, pentane, cyclooctane, toluene, benzene, and the like. Reaction temperature of from about −20° C. to 50° C. are preferred with 0° C. to 25° C. being most preferred. The reaction is conveniently carried out by placing the metal salt, the organic halide and the solvent in the reactor and then slowly adding the cyclopentadienyl ligand to the reaction mixture, with stirring.

The invention is further illustrated by, but is not intended to be limited to, the following examples.

EXAMPLE 1

Preparation of [(Me$_4$C$_5$) SiMe$_2$N-t-Bu]TiCl$_2$ at 0° C.

In a 100 mL Schlenk flask were placed 1.51 g of TiCl$_3$(THF)$_3$ (4.07 mmol), 20 mL of tetrahydrofuran, and 0.37 g of methylene chloride (4.4 mmol). The blue slurry was cooled to 0° C. in an ice-water bath and a solution of 1.80 g of [(Me$_4$C$_5$)SiMe$_2$N-t-Bu]Mg$_2$Cl$_2$(THF) (4.08) in 20 mL of tetrahydrofuran was added dropwise over 18 minutes. After the addition was complete, the reaction was kept cold for an additional 40 minutes and then allowed to warm to room temperature and stir overnight. The solvent was then removed in vacuo. The solids were extracted with approximately 30 mL of hexanes for 30 minutes and then the solids were removed by filtration through a medium frit. An internal standard was added and an aliquot of the amber colored filtrate was stripped to near dryness and redissolved in C$_6$D$_6$. $^1$H NMR confirmed the product's identity as pure [(Me$_4$C$_5$)SiMe$_2$N-t-Bu]TiCl$_2$. The yield was 96%.

EXAMPLE 2

Preparation of [(Me$_4$C$_5$)SiMe$_2$N-t-Bu]TiCl$_2$ at Ambient Temperature

In a 100 mL flask were placed 2.03 g of TiCl$_3$(THF)$_3$ (5.48 mmol), 18 mL of tetrahydrofuran, and 0.62 g. of methylene chloride (7.3 mmol). A solution of 2.39 g of [(Me$_4$C$_5$) SiMe$_2$N-t-Bu]Mg$_2$Cl$_2$(THF) (5.42 mmol) in 20 mL of tetrahydrofuran was added dropwise to the blue slurry of TiCl$_3$ over 14 minutes. The reaction had become warm to the touch. After 3 hours, the solvent was removed in vacuo. The solids were extracted with 50 mL of hexanes and filtered on a coarse frit. An aliquot of the filtrate was stripped to dryness and the orange-yellow solids redissolved in C$_6$D$_6$. $^1$H NMR confirmed the product's identity as fairly pure (83%) [(Me$_4$C$_5$)SiMe$_2$N-t-Bu]TiCl$_2$.

Comparison 1

THF Oxidation of Intermediate [(Me$_4$C$_5$)SiMe$_2$N-t-Bu]TiCl

In a 100 mL Schlenk flask was placed 2.00 g of TiCl$_3$(THF)$_3$ (5.4 mmol) and 15 mL of tetrahydrofuran. This blue slurry was cooled to 0° C. in an ice-water bath and a solution of 2.40 g of [(Me$_4$C$_5$)SiMe$_2$N-t-Bu]Mg$_2$Cl$_2$(THF) (5.44 mmol) in 20 mL of tetrahydrofuran was added dropwise over 17 minutes. After the addition was complete, a deep purple solution had formed. The reaction was allowed to warm to room temperature gradually. After stirring overnight, the reaction had turned a dark amber-brown color. The solvent was removed in vacuo. The solids were extracted with heptane and filtered through a coarse frit until the solution was colorless. An aliquot of the amber colored filtrate was stripped to dryness and redissolved in C$_6$D$_6$. The $^1$H NMR spectrum showed approximately a 25% yield of [(Me$_4$C$_5$)SiMe$_2$N-t-Bu]TiCl$_2$ and one major and some minor unidentified impurities. The diamagnetic products indicate that some oxidation has occurred, apparently by the THF solvent, without addition of the organic halide.

Comparison 2

Preparation of [(Me$_4$C$_5$)SiMe$_2$N-t-Bu]TiCl$_2$ at Ambient Temperature (Post Oxidation)

In a 100 mL flask were placed 2.01 g. of TiCl$_3$(THF)$_3$ (5.42 mmol) and 18 mL of tetrahydrofuran. A solution of 2.43 g of [(Me$_4$C$_5$)SiMe$_2$N-t-Bu]Mg$_2$Cl$_2$(THF) (5.51 mmol) in 20 mL of tetrahydrofuran was added dropwise to the blue slurry of TiCl$_3$(THF)$_3$. After stirring for 4 hours, the red-purple solution was oxidized with 0.67 g (5.61 mmol) of chloroform. The solution turned yellow-brown instantly. After stirring overnight, the solvent was removed in vacuo. A small amount of solids were triturated with deuterobenzene and the solution was filtered into a NMR tube. $^1$H NMR showed [(Me$_4$C$_5$)SiMe$_2$N-t-Bu]TiCl$_2$ in 60% purity.

What is claimed is:

1. A process for preparing a metallocene, said process comprising reacting a metal compound, wherein said metal has two oxidation states which are one oxidation unit apart and is selected from the group consisting of Group 4 to 9 metals, and actinide metals, with a magnesium halide salt of a cyclopentadienyl containing ligand in the presence of an organic halide oxidizing agent so as to form said metallocene while simultaneously raising the oxidation state of said metal.

2. The process of claim 1 wherein said metal compound has the formula MX$_n$ where M is the metal, n is an integer of from 1 to 6 and each X is independently an anionic ligand group or a neutral Lewis base ligand group having up to 30 non-hydrogen atoms.

3. The process of claim 1 wherein said organic halide is a $C_{1-12}$ alkylchloride.

4. The process of claim 1 wherein the reaction is carried out in a solvent comprising an ether.

5. The process of claim 4 wherein said solvent is selected from the group consisting of diethyl ether, 1,2-dimethoxyethane and tetrahydrofuran.

6. The process of claim 5 wherein said ether is tetrahydrofuran, said metal compound is TiCl$_3$(THF)$_3$, and said organic chloride is methylene chloride.

7. The process of claim 1 wherein said metal compound is a Ti(III) compound and a Ti(IV) containing metallocene is produced.

8. The process of claim 7 wherein said metallocene is [(Me$_4$C$_5$)SiMe$_2$N-t-Bu]TiCl$_2$.

9. The process of claim 2 wherein the metal is selected from the group consisting of Ti, V, Nb, Cr, Mo, W, Mn, Fe, Ru, Os, Co, Rh, Ir, Pa, and U.

* * * * *